United States Patent [19]

Little et al.

[11] Patent Number: 4,789,434

[45] Date of Patent: Dec. 6, 1988

[54] METHOD AND APPARATUS FOR MEASURING CORROSION CURRENT INDUCED BY MICROBIOLOGICAL ACTIVITIES

[75] Inventors: Brenda J. Little, Picayune, Miss.; Sol M. Gerchakov, deceased, late of Coral Gables, Fla., by Barbara J. Gerchakov, executrix

[73] Assignee: The United States of America as represented by the Secretary of the Navy, Washington, D.C.

[21] Appl. No.: 106,281

[22] Filed: Oct. 9, 1987

[51] Int. Cl.[4] .............................................. C12Q 1/02
[52] U.S. Cl. ................................. 204/1 T; 204/403; 204/404; 435/29; 435/291
[58] Field of Search ................... 204/1 C, 404, 403; 436/63; 435/29, 291, 817; 324/426; 429/2

[56] References Cited

U.S. PATENT DOCUMENTS 3,336,161 8/1967 Sutton et al. ..................... 429/2
3,502,559 3/1970 Alexander ....................... 429/2 X Primary Examiner—G. L. Kaplan
Attorney, Agent, or Firm—Thomas M. Phillips

[57] ABSTRACT

A corrosion measuring device is disclosed for measuring microbiologically induced corrosion using galvanically coupled electrodes exposed in an electrolytically continuous, biologically separated environment. The device consists of two, mirror image, half-cells separated by either a 0.1-$\mu$m porous cellulose acetate/cellulose nitrate membrane or a solid disc. The membrane is used when measuring total corrosion current in a chemically continuous environment while the solid disc is used when evaluating individual corrosion mechanisms in chemically isolated environment. Culture medium is pumped through inlets of the half-cells at a constant speed. One of the electrodes is inoculated with viable microorganisms which colonize the electrode surface creating a corrosion current that can be measured with a zero resistance ammeter. If a solid (Teflon) disc is used, an agar salt bridge is inserted through the utility port of each half-cell to maintain electrolytic continuity. In such a chemically separated environment, the biologically controlled mechanisms for corrosion can be evaluated, including, but not limited to differential aeration, acid production, or entrapment of metallic cations.

10 Claims, 3 Drawing Sheets

METHOD AND APPARATUS FOR MEASURING CORROSION CURRENT INDUCED BY MICROBIOLOGICAL ACTIVITIES

BACKGROUND OF THE INVENTION

1. Field of the Invention

The present invention relates to an apparatus and method for measuring the corrosion current induced by microbiological activities on a metal electrode using two galvanically coupled electrodes in dual cells which are electrolytically continuous, chemically continuous and biologically separated. The contributions of individual microbiological mechanisms can also be evaluated using the apparatus.

2. Description of the Prior Art

Over the last fifty years, microbiologists and corrosion engineers have been documenting the corrosive effects of microorganisms attached to metal surfaces in a variety of media. Despite this recognition and documentation, the quantification of the electrochemical impact of microorganisms and individual mechanisms for microbiologically induced corrosion has remained elusive because of the complexity of microbiological processes and lack of analytical techniques.

Attempts to measure microbiologically induced corrosion have been made using polarization techniques that are accurate only for general corrosion on homogeneous metal surfaces. Polarization techniques assume a metal is corroding by a Wagner-Traud mechanism, i.e., that anodic and cathodic processes occur with equal probability on all parts of the corroding metal surface. Metal surfaces colonized by microorganisms are not homogeneous and the resulting corrosion is localized, not general. Anodic and cathodic areas are distinct in space and stable in time. This invention allows a separation of anodic and cathodic areas.

Prior known corrosion measuring devices such as described in U.S. Pat. No. 3,605,151 to E. Schaschl et al and Japan Patent No. 59-48469 to Takashi Yamamoto have used techniques to separate anodic and cathodic areas to evaluate abiotic corrosion processes. However the prior art does not provide a means to maintain biological separation between the two electrodic areas. Neither apparatus biologically separates the electrolyte of the two cells, nor do they maintain a constant and measured flow of the electrolyte.

SUMMARY OF THE INVENTION

The present invention provides for a method and apparatus for measuring microbiologically induced corrosion current in metal electrodes. The invention uses two galvanically couple electrodes in dual cells which are biologically separated but electrolytically continuous with a constant and measured flow of electrolyte through the cells. The invention also provides for the evaluation of the individual mechanisms for microbiologically induced corrosion, by chemically separating the dual cells while maintaining electrolytic continuity.

Accordingly an object of the present invention is the provision of a method and apparatus for measuring biologically induced corrosion current in metal electrodes.

Another object of the invention is the provision of a method and apparatus for measuring biologically induced corrosion in metal electrodes using dual cells which are biologically separated but electrolytically and chemically continuous.

Still another object of the invention is the provision of a method and apparatus for measuring biologically induced corrosion in metal electrodes using dual cells which are biologically separated but electrolytically and chemically continuous with a constant and measured flow of electrolyte through the cells.

A further object of the invention is the provision of a means of evaluating the individual mechanisms for biologically induced corrosion currents in metals.

Other objects, advantages and novel features of the invention will become apparent from the following detailed description of the invention when considered in conjunction with the accompanying drawings.

DESCRIPTION OF THE PREFERRED EMBODIMENT

Figure 1:
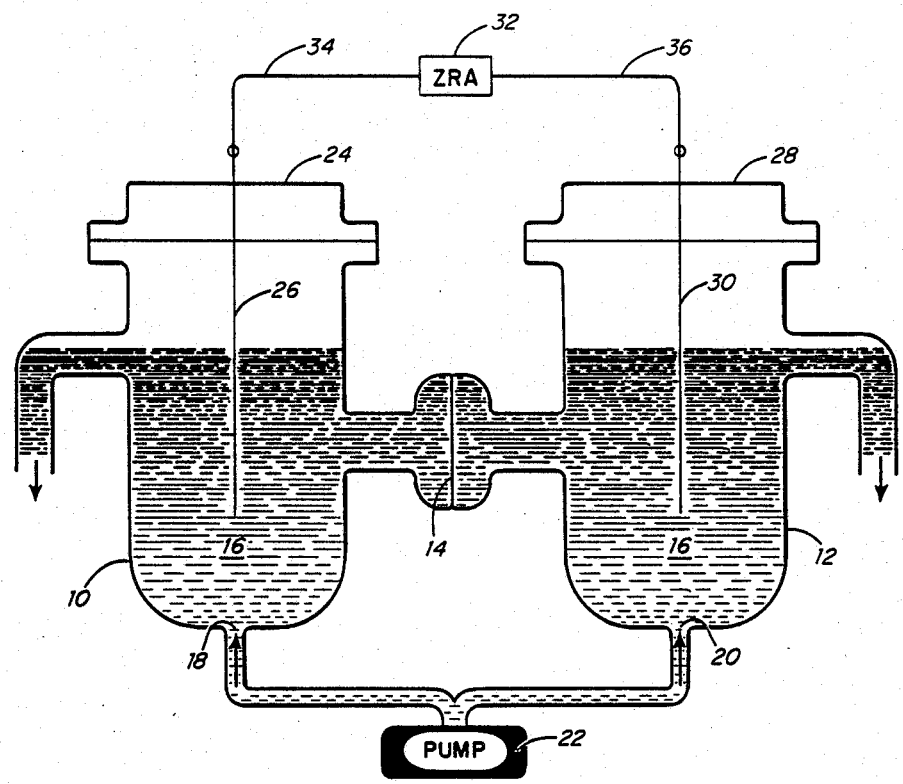
FIG. 1 is a schematic diagram, showing the preferred embodiment in its simplest form.

Referring now to the drawings wherein there is shown in FIG. 1, the measurement cell in simplified form. The cell comprises two halves, 10 and 12 which are mirror images of each other, separated by a 0.1 $\mu$m cellulose acetate/cellulose nitrate membrane 14. Membrane 14 is secured between the two half-cells 10 and 12, respectively, with a clamp (not shown) that also holds the two half-cells together. An electrolyte 16 is pumped from a reservoir (not shown) through inlets 18 and 20 at the bottom of half-cells 10 and 12, respectively, by means of a pump 22. Cell cover 24 is secured to half-cell 10 by means of a clamp (not shown) and supports electrode 26 which is immersed in electrolyte 16. Cell cover 28 is secured to half-cell 12 by means of a clamp (not shown) and supports electrode 30 which is immersed in the electrolyte 16. Electrodes 26 and 30 are connected to zero resistance ammeter 32 by means of electrical leads 34 and 36, respectively.

Figure 2:
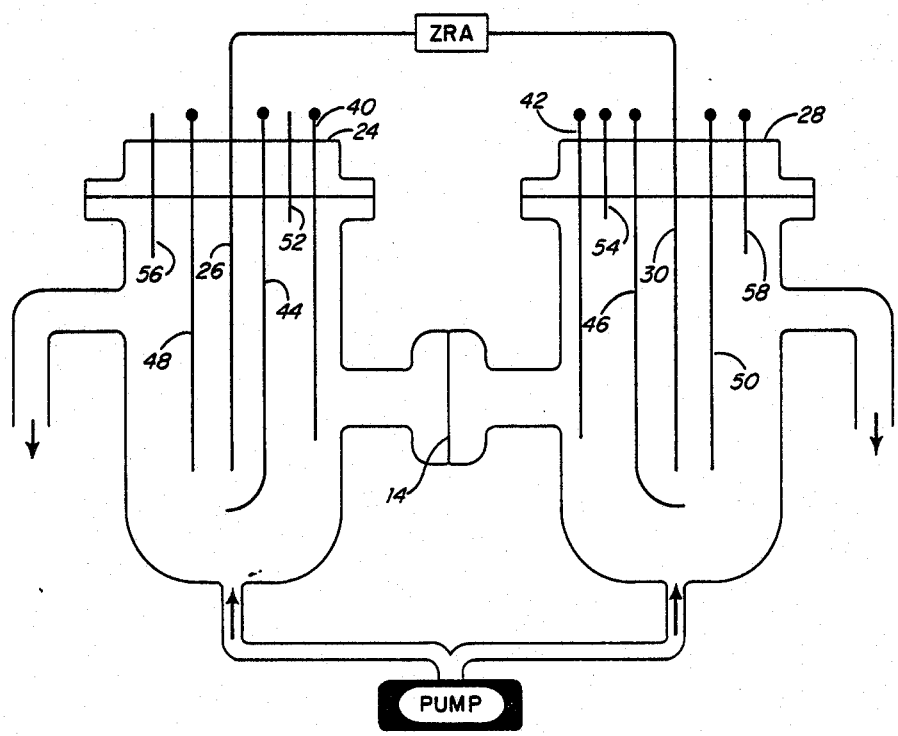
FIG. 2 is a schematic diagram of the preferred embodiment showing the corrosion measuring device with all its components.
Figure 3:
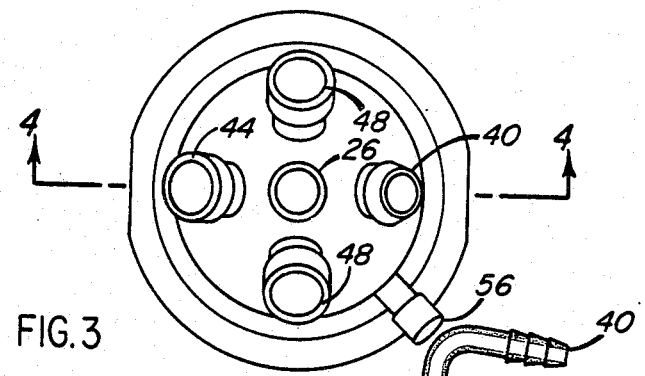
FIG. 3 is a plan view drawing of a half-cell of the actual apparatus used in practicing the invention.
Figure 4:
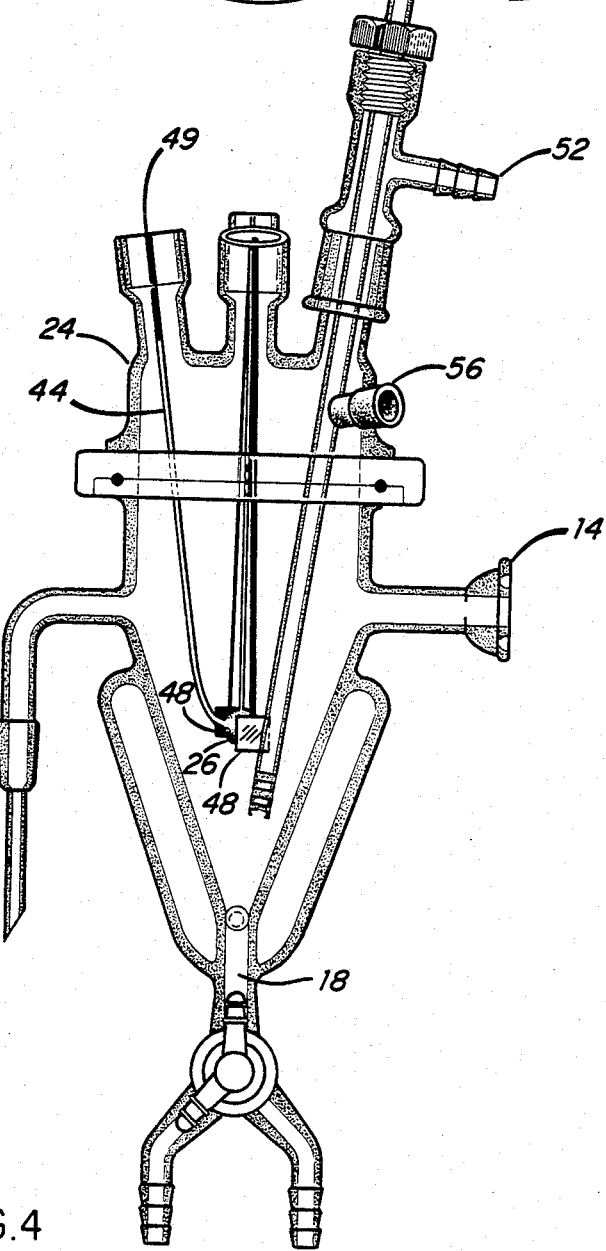
FIG. 4 is a cross-section of the half-cell of FIG. 3 taken along the lines 4—4.

As shown in FIG. 2, in addition to the working electrodes 26 and 30, Luggin capillaries 44 and 46 to contain reference electrodes (either hydrogen or saturated calomel) and counter electrodes 48 and 50 make it possible to read the individual half-cell potentials using a potentiostat when leads 34 and 36 are disconnected from the zero resistance ammeter 32. As shown in FIG. 4, Luggin capillary 44 containing a reference electrode 49 is positioned adjacent the working electrode 26. Counter electrode 48 is made of platinum and is divided so that Luggin capillary 44 and working electrode 26 are positioned between the two halves. The measured potential difference between the working and reference electrodes is $$E = \Delta\phi + \Delta_{contact} + \Delta\phi_{ref,e} - IR$$

where IR is the potential drop developed when the I overcomes the resistance $R = 7/\sigma A$ of the electrolyte between the working electrode 26 and the reference electrode in the Luggin capillary 44 by means of which the reference electrode 48 makes ionic or electrolytic contact with the working electrode 26.

As shown in FIG. 2 and 4, gas inlets 40 and 42 are positioned in such a way as to mix the contents in the half-cells adjacent to the membrane 14. Covers 24 and 28 also provide support for the metal specimen holders 26 and 30, Luggin capillaries 44 and 46 for reference electrodes 49, platinum counter electrodes 48 and 50, gas outlets 52 and 54, and utility ports 56 and 58.

Utility ports 56 and 58 are used for electrolyte sampling, inoculation of metal electrodes, and the insertion of an agar salt bridge for some applications. Inlets and outlets (liquid or gas) are provided with traps to prevent bacterial migration.

The effect of a (1) marine pseudomonad, an (2) obligate thermophilic filamentous bacterium, and an (3) iron-oxidizing stalked bacterium have been examined using the above described measurement cell. The bacterium designated B-3, a marine pseudomonad, (tentatively identified as *Pseudomonas waxmanii* sp. nov.) was isolated from a surface painted with a coating containing cuprous oxide and tributyl tin oxide and exposed in seawater. B-3 was maintained in marine broth as shown in Table 1.

TABLE 1

| Marine Broth | | | | |
|---|---|---|---|---|
| Peptone | 1.0 | g | Sodium bicarbonate | 0.032 g |
| Yeast extract | 0.2 | g | Potassium bromide | 0.016 g |
| Ferric citrate | 0.02 | g | Strontium chloride | 0.0068 g |
| Sodium chloride | 3.89 | g | Boric acid | 0.0044 g |
| Magnesium chloride dried | 1.18 | g | Sodium Silicate | 0.0008 g |
| Sodium sulfate | 0.65 | g | Sodium fluoride | 0.00048 g |
| Calcium chloride | 0.36 | g | Ammonium nitrate | 0.00032 g |
| Potassium chloride | 0.11 | g | Disodium phosphate | 0.0016 g |

*Thermus aquaticus,* an organism that requires temperatures from 60° to 80° C. for growth was isolated from a failed nickel 201 heat exchanger that had been maintained with distilled water at 60° C. The iron oxidizing bacterium was isolated from a ASTM 1018 cold-rolled mild steel water box that had been filled with naturally occurring estuarine water. *Thermus aquaticus* and the iron oxidizing bacterium were maintained in a basal salt medium as shown in Table 2. Standard microbiological techniques were used to isolate and maintain these organisms as pure cultures. The culture media were used as electrolytes for the corrosion measurements. Organisms that had a greater ability to attach to surfaces were selected by providing metal disks in the culture media. These disks were used for subsequent transfers and for inoculation of the electrolytes in the corrosion experiments.

TABLE 2

| Basal Salt Medium Stock Solution | | | | | | | | |
|---|---|---|---|---|---|---|---|---|
| A | | | B | | | C | | |
| NTA | 1.0 | g | FeCl | 0.28 | g | MnSO$_4$.H$_2$O | 0.22 | g |
| CaSO$_4$.2H$_2$O | 0.6 | g | Distilled H$_2$O | 1.0 | L | ZnSO$_4$.7H$_2$O | 0.05 | g |
| NaCl | 0.08 | g | H$_2$SO$_4$ (conc) | 0.50 | mL | H$_3$BO$_3$ | 0.05 | g |
| KNO$_3$ | 1.03 | g | | | | CuSO$_4$ | 0.0016 | g |
| NaNO$_3$ | 6.89 | g | | | | Na$_2$MoO$_4$.2HO | 0.0025 | g |
| Na$_2$HPO$_4$ | 1.11 | g | | | | CoCl$_2$.6H$_2$O | 0.0046 | g |
| Distilled H$_2$O | 1.0 | L | | | | H$_2$SO$_4$ | 0.50 | mL |
| Adjust pH to 8.2 with NaOH | | | | | | Distilled H$_2$O | 1.0 | L |

Final liquid medium: Combine and dilute to 1 L with distilled water 100 mL Solution A, 10 mL Solution B, 10 mL Solution C, and 0.25 g tryptone. Adjust the pH value to 7.6.

In operation, and by way of example, with the 0.1 μm membrane 14 in place, electrolyte 16 is continuous between the two half-cells 10 and 12 while they are biologically separated because microorganisms cannot move through membrane 14 between the two half-cells. To test for microbiologically induced corrosion, the two half-cells and the electrodes 26 and 30 are sterilized and then a sterilized electrolyte is pumped through the half-cells at a constant speed of about one milliliter per minute to provide a medium for a pre-selected microorganisms to grow. The two electrodes are then galvanically coupled and continuous readings of the current flow in ammeter 32 are recorded. In such a configuration, the electrodes are identical. In the absence of microbial colonization the measured current will be zero, because there is no potential difference between electrodes 26 and 30. Electrode 30 is then inoculated with the pre-selected culture of microorganisms and current measurements are recorded. These readings indicate whether an anodic or cathodic reaction is taking place on the inoculated electrode 30 as a result of microbial colonization. If the microorganisms are forcing an oxidation, electrode 30 becomes an anode; a reduction causes electrode 30 to become a cathode.

Figure 5:
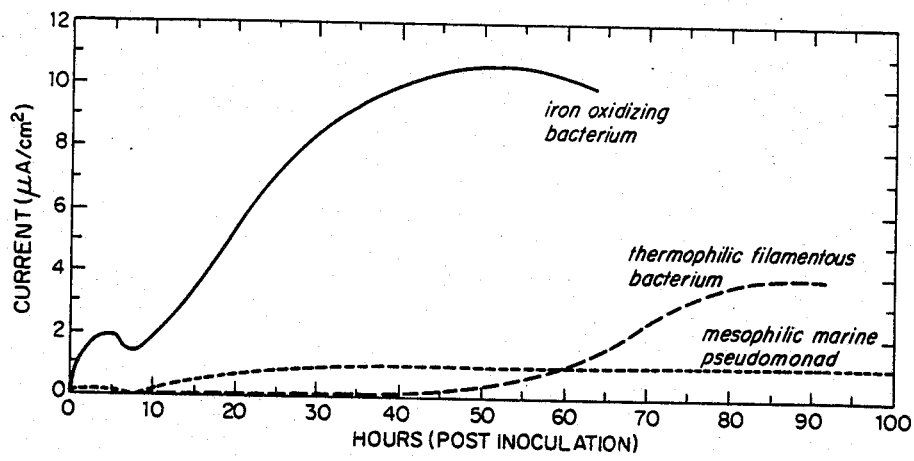
FIG. 5 is a graph showing corrosion current vs time induced by three bacterial species.

In all three evaluations, the metal in the cell inoculated with bacteria became the anode of the couple, with currents ranging from 1.0 to 10.4 μA cm$^{-2}$. These are shown in FIG. 5. The optimum growth temperature for *Thermus aquaticus* is 60° to 70° C., and the organism is completely inactive below 50° C. The dual compartment cell holding nickel 201 specimens was submerged in a water bath maintained at 60° C., and one compartment was inoculated with the organism. After ~20 hours, the current at the inoculated electrode began to increase anodically and finally stabilized at 3.8 μA cm$^{-2}$. At ambient temperature, where *Thermus aquaticus* is inactive, no current was observed. Similar observations were made when the organisms colonizing the nickel electrode were heat killed. These results suggest that these particular organisms must be metabolically active to affect the corrosion of nickel 201.

Bacterium B-3 was inoculated into one half cell holding a copper electrode coupled to an uninoculated copper electrode. After a 10 hour incubation time at ambient temperature, the current at the inoculated electrode began to increase anodically to ~1.0 $\mu A$ $cm^{-2}$. Similar results were obtained when the stalked iron-bacterium was inoculated into one half of the system containing coupled mild steel electrodes. An anodic current of 10.4 $\mu A$ $cm^{-2}$ was measured after ~40 hours. The iron oxidizing bacteria on the mild steel surface produced tubercles of ferric hydroxide. When these microorganisms were heat killed, the anodic current remained stable at 8.6 $\mu A$ $cm^{-2}$. The tubercles formed by the microorganism prevented diffusion to and from the surface and created differential aeration cells that were independent of the biochemical activities of the bacteria.

Individual mechanisms for microbiologically induced corrosion cannot be evaluated in the presence of microorganisms because the microbes are impacting the metal surface via numerous mechanisms simultaneously. Instead, the individual mechanisms must be defined in chemical terms and quantified abiotically.

Several possible mechanisms have been proposed for microbial effects on corrosion under aerobic and microaerobic conditions. Among these are the (1) formation of differential concentration (aeration) cells between areas covered by bacteria and bare areas, (2) production of acids by microorganisms, and (3) entrapment of metallic cations by microbiologically produced polymeric material. With the aid of the two compartment cell described above, it is possible to abiotically simulate conditions to evaluate the proposed mechanisms individually.

When the apparatus is used as a means of evaluating the contributions of individual microbiological mechanisms, cellulose membrane 14 is replaced with a solid membrane which may be made of Teflon to chemically isolate the two half-cells. Electrolytic continuity is then maintained with an agar salt bridge inserted through the utility port 56 and 58 into the electrolyte 16 of each of the half-cells.

Three individual mechanisms for microbiological induced corrosion have been evaluated using three different metals. As stated above, the 0.1 $\mu m$ filter was replaced with a Teflon disc to ensure chemical separation of the compartments, The impacts of differential aeration, acetic acid, and entrapped metal cations were quantified using copper, nickel, and mild steel electrodes in a 3% synthetic salt solution (Table 3). Platinum electrodes were used as chemically unreactive surfaces with which to compare the electrochemical responses of the other metals.

The cells were assembled with pairs of 1-$cm^2$ flat circular electrodes [copper (99% pure Martz grade), nickel 201, and ASTM 1018 mild steel] sterilized and connected to the zero resistance ammeter 32. The commercially available EG & G Model 350 corrosion Measurement System was used by making the connections to the electrodes so that the measurement system functioned as a zero resistance ammeter.

TABLE 3

| Major Ionic Components of 3% Synthetic Salt solution | | |
|---|---|---|
| Ion | | PPT |
| Chloride | ($Cl^-$) | 1.658 |
| Sodium | ($Na^+$) | 0.920 |
| Sulfate | ($SO_4^=$) | 0.227 |
| Magnesium | ($Mg^{++}$) | 0.112 |
| Calcium | ($Ca^{++}$) | 0.035 |

TABLE 3-continued

| Major Ionic Components of 3% Synthetic Salt solution | | |
|---|---|---|
| Ion | | PPT |
| Potassium | ($K^+$) | 0.033 |
| Bicarbonate | ($HCO_3$) | 0.013 |

Under sterile conditions, oxygen was bubbled through both compartments of the cell until the current stabilized at zero. Differential aeration was created by replacing the oxygen in one of the compartments with nitrogen. The impact of acidic metabolites was evaluated by making one of the compartments 10 mM with respect to acetic acid. Two experiments were designed to quantify the impact of metal cations on the corrosion of metal electrodes. In one experiment containing copper electrodes and purged with nitrogen, 1.2 mM Cu(II) was added to one compartment. In another experiment containing nickel 201 electrodes purged with air, 6.6 mM Fe(III) was added to one compartment.

At room temperature, differential aeration created anodes of the oxygen-depleted mild steel and copper-nickel electrodes. No current was observed with platinum and nickel electrodes.

Figure 6:
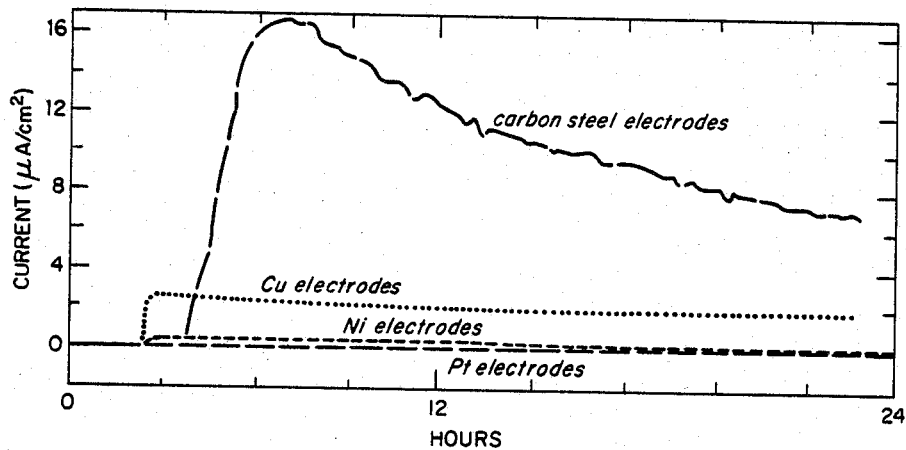
FIG. 6 is a graph showing impact of 10 mM acetic acid on corrosion current vs time for nickel, copper, carbon steel, and platinum electrodes.

Most heterotrophic bacteria secrete organic acids during the fermentation of organic substrates. Organic acids from bacteria have been shown to enhance the corrosion of the number of different metal types. The types and amounts of acids produced in nature depends on the kinds of organisms present and the substrate molecules available. However, in natural microaerobic habitats, acetic acid is the major organic acid produced during fermentation. In all cases, the electrodes in the compartment containing 10 mM acetic acid became the anodes of the two-compartment apparatus, with currents that stabilized at 0.1, 1.8, and 7.5 $\mu A$ $cm^{-2}$, respectively, for nickel, copper, and mild steel. The current between the platinum electrodes remained stable at 0 $\mu A$ $cm^{-2}$ for 24 hours beyond the end of the experiment as shown by the graph of FIG. 6.

Figure 7:
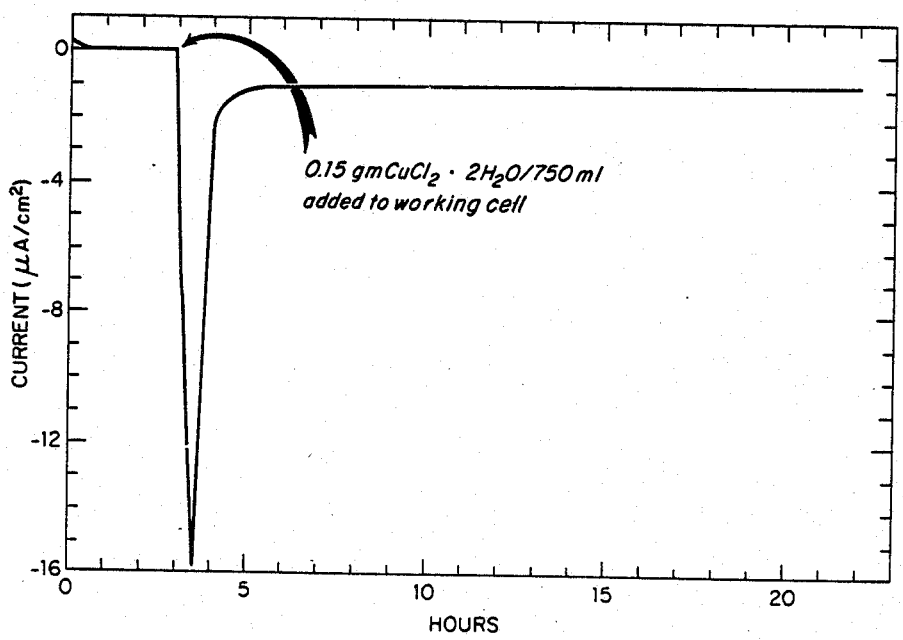
FIG. 7 is a graph showing cathodic corrosion current vs time for a copper electrode in the presence of 1.2 mM cupric ion.

Microorganisms colonizing surfaces secrete extracellular polymers capable of entrapping metals. The impact of the entrapped metal cations on corrosion is a function of the oxidation/reduction potential of the entrapped cation, the oxidation/reduction of the metal substratum, pH value, partial pressure of oxygen, etc. This is demonstrated when the cell holding copper electrodes and purged with nitrogen. When 1.2 mM Cu(II) was added to one compartment, it immediately became the cathode, with a stable cathodic current of 1.8 $\mu A$ $cm^{-2}$ as shown in the graph of FIG. 7. The potential shifted from $-0.236$ to $-0.170$ V (saturated calomel electrode) during this reaction. The cathodic current can be attributed to one or both of the following reactions based on potential measurements made with the 3-electrode system:

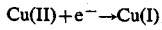

$$Cu(II) + e^- \rightarrow Cu(I)$$

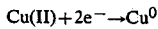

$$Cu(II) + 2e^- \rightarrow Cu^0$$

In another abiotic simulation experiment, a cell holding nickel 201 specimens was purged with air. When 6.6 mM Fe(III) was added to one of the compartments, the electrode in that compartment became anodic, with a current of 0.3 $\mu A$ $cm^{-2}$. In this case, the anodic current probably results from oxygen displacement at the nickel surface with a weaker electron acceptor in the form of some $Fe^{+3}$ complex.

Obviously many modifications and variations of the present invention are possible in light of the above teachings. It is therefore to be understood that within the scope of the appended claims the invention may be practiced otherwise than as specifically described.

We claim:

1. A corrosion measuring apparatus including in combination:
   a vessel containing an electrolyte,
   means within said vessel to divide said vessel into two cells which are in electrolyte and chemical communication with one another and biologically separated from one another,
   each of said cells having support means for supporting a sample metal in said electrolyte,
   a microorganism in one of said cells, each of said cells having an inlet port and outlet port for providing a continuous and measured flow of the electrolyte through the two cells,
   means being connected between said support means for measuring current flow which is proportional to corrosion of a metal sample induced by said microorganism.

2. The corrosion measuring apparatus of claim 1 wherein said means to divide said vessel is a porous membrane having openings no greater than 0.1 micron.

3. The corrosion measuring apparatus of claim 2 wherein said porous membrane is cellulose acetate/cellulose nitrate.

4. The corrosion measuring apparatus of claim 1 wherein said electrolyte is basal salt solution.

5. The corrosion measuring apparatus of claim 1 wherein said means to measure current flow includes a zero resistance ammeter.

6. A corrosion measuring apparatus including in combination:
   a vessel containing an electrolyte,
   means within said vessel to divide said vessel into two cells which are biologically and chemically separated from one another,
   coupling means between said cells to maintain electrolytic continuity between the cells,
   each of said cells having support means for supporting a sample metal in said electrolyte,
   counter and reference electrodes being disposed in each of said cells to provide a means to measure the potential between the sample metal and reference electrodes in the individual half-cells,
   means being connected between said electrodes for measuring current flow which is a measure of the corrosion caused by the chemical environment.

7. The measuring apparatus of claim 6 wherein said means to divide said vessel is a solid membrane.

8. The measuring apparatus of claim 6 wherein said coupling means is an agar salt bridge.

9. A method of evaluating the electrochemical impact of microbiological species on metal electrodes comprising the steps of:
   providing a first cell of electrolyte,
   providing a second cell of electrolyte in electrolytic communication and biologically isolated from said first cell,
   providing a continuous and measured flow of the electrolyte through the two cells,
   disposing a metal electrode in each of said cells,
   electrically connecting said electrodes to provide for the flow of current therebetween,
   inoculating one of said electrodes with a microorganism, and
   observing the current flow between said electrodes as an indication of the corrosion induced by said specimen microorganism on said inoculated electrode.

10. A method of evaluating the electrochemical impact of microbiological species on metal electrodes comprising the steps of:
    providing a first cell of sterilized electrolyte,
    providing a second cell of sterilized electrolyte in electrolytic communication and biologically isolated from said first cell,
    providing a continuous and measured flow of the sterilized electrolyte through the two cells,
    disposing a metal electrode in each of said cells
    said electrodes being substantially identical,
    galvanically coupling said electrodes to provide for a flow of current therebetween,
    inoculating one of said electrodes with a microorganism,
    observing the current flow between said electrodes as an indication of the corrosion induced by said specimen microorganism.

* * * * *